(12) United States Patent
Nieberding

(10) Patent No.: US 9,827,442 B2
(45) Date of Patent: Nov. 28, 2017

(54) THERMOPLASTIC SHEET, A RADIATION MASK OF THERMOPLASTIC SHEET AND METHOD FOR PROVIDING SAID SHEET AND SAID MASK

(75) Inventor: Reginald Nieberding, Kapellen (BE)

(73) Assignee: T TAPE COMPANY BV, Putte (NL)

( * ) Notice: Subject to any disclaimer, the term of this patent is extended or adjusted under 35 U.S.C. 154(b) by 819 days.

(21) Appl. No.: 14/117,715

(22) PCT Filed: Jun. 19, 2012

(86) PCT No.: PCT/EP2012/061667
§ 371 (c)(1),
(2), (4) Date: Nov. 14, 2013

(87) PCT Pub. No.: WO2012/175477
PCT Pub. Date: Dec. 27, 2012

(65) Prior Publication Data
US 2014/0206924 A1   Jul. 24, 2014

(30) Foreign Application Priority Data
Jun. 20, 2011 (EP) .................................. 11170625

(51) Int. Cl.
| | | |
|---|---|---|
| A61N 5/10 | (2006.01) | |
| A61L 31/04 | (2006.01) | |
| B29C 67/24 | (2006.01) | |
| C08J 3/22 | (2006.01) | |
| C08J 5/18 | (2006.01) | |
| C08L 67/04 | (2006.01) | |
| A61B 90/18 | (2016.01) | |
| A61B 90/14 | (2016.01) | |
| C08K 3/34 | (2006.01) | |
| C08K 5/00 | (2006.01) | |
| C08L 25/12 | (2006.01) | |

(52) U.S. Cl.
CPC ............ *A61N 5/1001* (2013.01); *A61B 90/14* (2016.02); *A61B 90/18* (2016.02); *A61L 31/041* (2013.01); *A61N 5/1049* (2013.01); *B29C 67/24* (2013.01); *C08J 3/226* (2013.01); *C08J 5/18* (2013.01); *C08L 67/04* (2013.01); *A61N 2005/1097* (2013.01); *C08J 2367/04* (2013.01); *C08J 2467/00* (2013.01); *C08K 3/346* (2013.01); *C08K 5/0025* (2013.01); *C08L 25/12* (2013.01)

(58) Field of Classification Search
CPC ................................... C08L 67/04; C08L 9/02
See application file for complete search history.

(56) References Cited

U.S. PATENT DOCUMENTS

| | | | |
|---|---|---|---|
| 4,252,516 A | * | 2/1981 | Raley .................... B29C 51/225 425/290 |
| 4,661,535 A | | 4/1987 | Borroff et al. |
| 5,816,797 A | | 10/1998 | Shoenfeld |
| 2004/0133102 A1 | | 7/2004 | Uematsu |

FOREIGN PATENT DOCUMENTS

| | | |
|---|---|---|
| GB | 2125803 A | 3/1984 |
| JP | 01-197548 A | 8/1989 |
| JP | 2005-8892 A | 1/2005 |

OTHER PUBLICATIONS

McMaster "Aspects of Polymer-Polymer Thermodynamics", Macromolecules, 1973, vol. 6, No. 5, pp. 760-773.*
International Search Report and Written Opinion of the International Searching Authority for International Application No. PCT/EP2012/061667, dated Jul. 20, 2012.
Extended European Search Report issued in European Patent Application No. 11170625.5, dated Oct. 4, 2011.
Office Action issued in European Patent Application No. 11170625.5, dated Aug. 16, 2013.

* cited by examiner

*Primary Examiner* — Peter F Godenschwager
(74) *Attorney, Agent, or Firm* — Knobbe, Martens, Olson & Bear LLP

(57) ABSTRACT

The present invention relates to a thermoplastic composition suitable for manufacturing a thermoplastic sheet for producing a medical cast, such as a radiation mask. The composition has a polymeric component comprising a mixture of a styrene acrylonitrile copolymer and polycaprolactone, optionally together with a cross-linker and/or a filler, wherein the polymeric component comprises, 20 to 40 weight % of a styrene acrylonitrile copolymer and 80 to 60 weight % of a polycaprolactone, expressed in weight % of the polymeric component, wherein the thermoplastic composition has a glass transition temperature of 35° C.-80° C. The invention further relates to a thermoplastic sheet and to a medical cast, in particular a radiation mask, obtainable from said composition. In a final aspect, the invention relates to a method for producing said sheet and said radiation mask.

25 Claims, No Drawings

THERMOPLASTIC SHEET, A RADIATION MASK OF THERMOPLASTIC SHEET AND METHOD FOR PROVIDING SAID SHEET AND SAID MASK

CROSS-REFERENCE TO RELATED APPLICATIONS

This application is the U.S. National Phase under 35 U.S.C. §371 of International Application PCT/EP2012/061667, filed Jun. 19, 2012, which claims priority to EP 11170625.5, filed Jun. 20, 2011.

FIELD OF THE INVENTION

The present invention provides a thermoplastic composition suitable for manufacturing a thermoplastic sheet. The compositions and sheets provided by the invention are particularly useful for making medical casts, particularly for radiation masks.

The medical casts of the invention are particularly suitable for immobilizing at least part of a subject's body part for receiving radiation treatment. The invention is suitable for use in the medical field, particularly for immobilization purposes in radiotherapy and cancer treatment.

BACKGROUND

Immobilization devices such as a cast, a splint, a brace (orthosis) and stiffening apparatuses are used to impart a desired position to a portion of the body or to immobilize the supported portion relative to other parts of the body. Traditionally, plaster casting materials have been used because they are very low cost. However, plaster casting materials are heavy and cannot be cleaned or easily removed.

Recently, plaster casting materials have been replaced by synthetic casting materials which are lighter in weight and can be cleaned but have a rough exterior surface and are still relatively heavy and bulky. These materials are irritating to sensitive skin areas such as to facial skin.

Thermoplastic materials have been introduced for forming casts and braces and immobilization devices such as used in radiation therapy. Thermoplastic materials with high melting point preclude the possibility of moulding directly on a patient's skin as severe burns would result. These materials require the use of positive casts of the targeted part, to allow moulding and the use of large ovens for softening the sheets. The construction of positive casts is a particularly laborious and time consuming process.

These thermoplastic materials can be produced in extruded sheets which, when brought to a melt point temperature of 50° C. to 100° C., can be molded and manipulated to conform to and shape around a body part, such as a limb, and then allowed to cool to hardness. These materials can also be reheated, brought back to their original shape and then remolded into a different shape. Compared to other casting materials, the thermoplastic materials provide many advantages including simplicity of use and ease of cleaning. However, to be able to mold the material a temperature is required above the temperature which a sensitive skin such as facial skin can endure without damage.

Patients being treated by radiotherapy for a tumorous growth are typically required to receive radiation doses at regular intervals, whereby each dose should be precisely directed to the same location of the body. This necessitates immobilization materials and devices that are adapted to the shape of the body portion being treated.

However, a problem associated with the above-mentioned materials and devices made of thermoplastic material are that they lack flexibility. Another problem is that they are relatively heavy. Moreover, most materials are opaque, hence non-transparent. As a consequence, they do not permit observing the skin covered by it, nor do they permit adjusting the positioning of the material using markers present on one or both of the immobilization device and the covered body part.

The material for the manufacturing of casts for immobilization devices is preferably molded directly to the body part that needs to be immobilized prior to receiving radiotherapy. However, most casts are standardized so that there is some space between the body part in need of immobilization and the cast used thereto. This is problematic to accurately and quickly align the radiation source with the location of the tumor. This is especially problematic in the treatment of brain tumors where misalignment of the beam of radiation may cause brain damage.

A wide variety of plastic materials is known in the art for fixation or immobilization devices. Amongst those plastic materials, only a limited number have a sufficient formability and elasticity in the molten state at a temperature which can be supported by the body, to permit direct molding on a patient's body. Direct molding to the patient's body is important, as it permits adapting the size and shape of the immobilization device directly to each individual patient, in the position in which the body part is to be immobilized.

Moreover, most materials are not suitable for application to skin, especially not to soft skin such as facial skin. In addition, thermoplastic materials for immobilization devices or assemblies are quite rigid and hard upon crystallization when cooling down from the melting temperature. Consequently, the immobilization devices produced from these thermoplastic materials easily break in case of hard handling or after falling, which is a serious disadvantage.

There is thus a need for casting materials with improved properties. The invention therefor aims to provide a thermoplastic composition for forming a cast, resultant casts, and methods related thereto, that provide a solution to at least one of the problems previously mentioned.

SUMMARY OF THE INVENTION

The invention thereto provides a thermoplastic composition for forming a cast such as a radiation mask having a polymeric component comprising a mixture of a styrene acrylonitrile copolymer and polycaprolactone, optionally together with a cross-linker and/or a filler, wherein the polymeric component comprises, 20 to 40 weight % of a styrene acrylonitrile copolymer and 80 to 60 weight % of a polycaprolactone, expressed in weight % of the polymeric component, wherein the thermoplastic composition has a glass transition temperature of 35° C.-80° C.

In a preferred embodiment, the filler is talc.

In a preferred embodiment, the cross-linker is triallylcyanurate.

In a second aspect, the invention provides a thermoplastic sheet comprising a composition according to an embodiment of the invention, with a shore D hardness of 10-30.

In a preferred embodiment, the thermoplastic sheet has a thickness of 0.5 mm to 4 mm, preferably of 1 mm to 3 mm, more preferably of 1 mm to 2 mm.

In a preferred embodiment, the thermoplastic sheet is transparent.

In a preferred embodiment, the thermoplastic sheet is provided with perforations, preferably in a regular pattern.

This is advantageous as the perforations will reduce and/or avoid the patient some uncomfortable feelings such as sweating while the sheet of thermoplastic material is placed, for a certain time, on at least a part of his body.

The thermoplastic sheets of the invention have improved molding properties. It ensures that medical casts can be manufactured that correspond form-matching to the body part that needs to be immobilized.

In a further aspect, the invention provides a medical cast obtainable from a thermoplastic sheet according to an embodiment of the invention. In particular, the invention provides a radiation mask for delivering radiotherapy to a subject in need thereof, obtainable from a thermoplastic sheet according to an embodiment of the invention.

In a preferred embodiment a radiation mask is provided with a shore D hardness at least twice, preferably at least three times, the shore D hardness of the thermoplastic sheet.

A casts according to an embodiment of the invention has improved elasticity. Good elastic properties allow the cast after a deformation occurred, to return to the shape acquired after molding and crystallization on the patient's body part to be immobilized. This avoids breakage of the immobilization device.

In a preferred embodiment, the thermoplastic sheet or radiation mask comprises an identification element, such as a radio frequency identification tag. This is advantageous as it allows storage of information such as a patient's identity or medical record data. It assures that the right treatment is applied to the patient.

In a further aspect, the invention provides a method for the preparation of a thermoplastic sheet according to an embodiment of the invention, comprising:—mixing 20 to 40 weight % styrene acrylonitrile copolymer with 80 to 60 weight % polycaprolactone thereby providing a polymeric component, -optionally adding to the polymeric component a first filler, -granulating said polymeric component optionally together with the first filler thereby providing a first granulate, -adding to the first granulate a polycaprolactone granulate and optionally a cross-linker and/or a second filler, -bringing the resulting mixture under the action of pressure or heat or both in the form of a thermoplastic sheet, and -optionally perforating the thermoplastic sheet.

In a preferred embodiment of the method, the thermoplastic composition comprises 0.05-5% of filler and/or 0.05%-5% cross-linker. Preferably the filler is talc and the cross-linker is triallylcyanurate.

Use of a filler and/or cross-linker is advantageous as they enhance the processability of the composition and resulting sheet and provide improved toughness to a sheet of thermoplastic material. This has for effect that a thermoplastic sheet from a composition comprising a filler and/or cross-linker is fortified so that a sheet when warmed in a water bath, will be more easily transportable and breakage of the warm sheet due to sagging is reduced.

In a further aspect, the invention provides a thermoplastic composition obtainable or obtained by a method according to an embodiment of the invention, wherein the thermoplastic composition has a glass transition temperature between 30° C. and 80° C., preferably between 45° C. and 70° C., more preferably between 55° C. and 65° C.

In a final aspect, the invention provides a method for manufacturing a radiation mask for delivering radiotherapy to a subject in need thereof, comprising the steps of: —providing a thermoplastic composition according to any of claims 1-3 in the form of a sheet, —warming the sheet above its glass transition temperature thereby providing a sheet that is stretchable, —stretching the stretchable sheet to obtain a stretched sheet with a surface area at least double, preferably at least three times, the surface area of the stretchable sheet, —applying the stretched sheet to at least part of the subject's body in need of radiotherapy thereby deforming the stretched sheet into a shape conforming to the part of subject's body, -cooling the deformed sheet to ambient temperature to rigidify the deformed sheet and provide the radiation mask.

DETAILED DESCRIPTION OF THE INVENTION

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the present invention.

As used herein, the following terms have the following meanings: "A", "an", and "the" as used herein refers to both singular and plural referents unless the context clearly dictates otherwise. By way of example, "a compartment" refers to one or more than one compartment.

"About" as used herein referring to a measurable value such as a parameter, an amount, a temporal duration, and the like, is meant to encompass variations of +/−20% or less, preferably +/−10% or less, more preferably +/−5% or less, even more preferably +/−1% or less, and still more preferably +/−0.1% or less of and from the specified value, in so far such variations are appropriate to perform in the disclosed invention. However, it is to be understood that the value to which the modifier "about" refers is itself also specifically disclosed.

"Comprise," "comprising," and "comprises" and "comprised of" as used herein are synonymous with "include", "including", "includes" or "contain", "containing", "contains" and are inclusive or open-ended terms that specifies the presence of what follows e.g. component and do not exclude or preclude the presence of additional, non-recited components, features, element, members, steps, known in the art or disclosed therein.

The recitation of numerical ranges by endpoints includes all numbers and fractions subsumed within that range, as well as the recited endpoints.

The expression "% by weight" (weight percent), here and throughout the description unless otherwise defined, refers to the relative weight of the respective component based on the overall weight of the formulation.

The present invention relates to a thermoplastic composition, in particular to a thermoplastic composition suitable for forming a cast, preferably a medical cast that is part of an immobilization device, more preferably for immobilization of at least a part of a body of a subject in need of radiotherapy.

In particular, the invention provides a thermoplastic composition suitable for making improved thermoplastic sheets and radiation masks made thereof.

The thermoplastic composition of the invention comprises a polymeric component of styrene acrylonitrile copolymer and polycaprolactone.

Styrene acrylonitrile copolymer comprises styrene and acrylonitrile monomers. It is obtained from copolymerization of these monomers according to techniques known to a person skilled in the art. Styrene acrylonitrile copolymer is available as a commercial product. A styrene acrylonitrile copolymer suitable for use in the invention is for instance marketed under the trade name Luran (BASF Corporation, Mount Olive, N.J.) or Kostil (Polimeri Europa).

Preferably the styrene acrylonitrile copolymer has a processing temperature between 200 to 250° C. and a mold temperature between 40 to 80° C.

Luran® is selected from the group of Luran® 358 N, Luran® 368 R, Luran® 378 P, Luran® 388 S, Luran® HH-120, Luran® 378 P G7, Luran® CC 358N, Luran® CC 368R, Luran® CC 348Q.

In a preferred embodiment the styrene acrylonitrile copolymer used in the invention is Luran® 348 Q. This styrene acrylonitrile copolymer has the following mechanical properties: tensile modulus of 3600 MPa and tensile stress of 70 MPa, as measured by test method ISO 527-2 at 23° C. It is a highly transparent grade with light natural colour.

Polycaprolactone is well-known in the art. It is a biodegradable polyester. It is obtainable by ring opening polymerization of ∈-caprolactone using a suitable catalyst. Preferably the polycaprolactone used in the invention is poly-∈-caprolactone.

Polycaprolactone is available as a commercial product. A polycaprolactone preferred for use in the invention is marketed under the trade name CAPA 6500 and CAPA 6500C (Perstorp), which is poly-∈-caprolactone with 1,4-butanediol. Preferably the polycaprolactone is transparent. It is further preferred that the polycaprolactone has a molecular weight of around 50000.

The proportion of styrene acrylonitrile copolymer to polycaprolactone is important if suitable physical properties are to be attained. Preferably, the weight proportions of styrene-acrylonitrile copolymer to polycaprolactone are 1:4 to 2:3.

Preferably the polymeric component comprises 20 to 40 weight % of a styrene acrylonitrile copolymer and 80 to 60 weight % of a polycaprolactone, more preferably the polymeric composition comprises 30 weight % of a styrene acrylonitrile copolymer and 70 weight % of a polycaprolactone. The weight percentages indicated above are expressed in weight % of the polymeric component. Hence, they are compared to the sum of styrene acrylonitrile copolymer and polycaprolactone.

Small proportions of other materials, whether further copolymers included in or with the styrene-acrylonitrile copolymer, or in or with the polycaprolactone, or monomeric materials included in he polymer or copolymer chain or as additions may be allowable or even beneficial to the practice of this invention.

Optionally the polymeric component is combined with a cross-linker and/or filler. This has for effect that additional reinforcement is provided to the composition during heat-treatment.

In a preferred embodiment, the filler is a mineral filler. As mineral filler the following materials are suitable for use in the invention: talc, calcium carbonate, glass fiber. Preferably the filler is talc, more preferably medical grade talc. Medical talc is has the advantage that it is asbestos-free, brucite-free and of controlled particle size. The composition of the talc preferably is 95% talc as hydrated magnesium silicate. The empirical formula of talc is is Mg3 Si4 010 (OH)2 with a molecular weight of 379.3.

More preferably, a thermoplastic composition according to an embodiment of the invention comprises 0.05-5 weight % talc, preferably 0.05-5 weight % medical grade talc.

Talc improves extrusion output, quality and shortens the cycle times in thermoforming. Use of talc in the formulation reduces the stickiness of the polymer composition such that a patient's skin and hair are not sticking to a cast when molded on the patient's body.

The use of the naturally occurring mineral filler talc offers more possibilities for directing the characteristics of the product, for example further reduction of the coefficient of linear thermal expansion (CLTE) of the polymer composition.

The term "coefficient of linear thermal expansion" describes by how much a material will expand for each incremental change in temperature, as given by the formula $$a = \frac{dl}{l_0 \times dT}$$

where: dl=the change in length of material in the direction being measured, $l_0$=initial length of material in the direction being measured, and dT=the change in temperature over which dl is measured. Coefficients of linear thermal expansion can be measured by techniques known to a person skilled in the art. Coefficients of linear thermal expansion may for instance be determined with a silica dilatometer according to ASTM D 696 or ISO 1 1359.

In a preferred embodiment, the styrene acrylonitrile copolymer and the polycaprolactone have a coefficient of linear thermal expansion of 70 μm/(m.° C.) measured at a temperature of 20° C.

In a preferred embodiment, the cross-linker is triallylcyanurate. Triallylcyanurate, abbreviated as TAC, is known under the chemical name 2,4,6-Tris(2-propenyloxy)-1,3,5-triazine. Its molecular formula is C12H15N3O3; its molecular weight 249.27. More preferably, a thermoplastic composition according to an embodiment of the invention comprises 0.05-5 weight % cross-linker, more preferably 0.05-5 weight % triallylcyanurate. Most preferably an amount of about 1% triallylcyanurate is used in a composition according to an embodiment of the invention. Use of the trifunctional cross-linker can improve the strength and thermostability of the cast.

A thermoplastic composition according to an embodiment of the invention have a glass transition temperature of 35° C.-80° C., preferably 45° C.-70° C., more preferably 55° C.-65° C., most preferably around 60° C.

By "glass transition temperature", abbreviated $T_g$, as used herein, it is meant the temperature at which an amorphous material transitions between a molten or rubber-like state into a hard and relatively brittle state.

Preferably a thermoplastic composition obtainable or obtained by a method according to the invention has a glass transition temperature between 30° C. and 80° C., preferably between 45° C. and 70° C., more preferably between 55° C. and 65 ° C., most preferably around 60° C.

A thermoplastic composition according to an embodiment of the invention can advantageously be used for the manufacturing of thermoplastic sheets. The terms "sheet of thermoplastic material" and "thermoplastic sheet" are used as synonyms.

A sheet comprising a thermoplastic composition according to an embodiment of the invention can be obtained by bringing the thermoplastic composition under the action of pressure or heat or both into a deformable state and to form a sheet.

A sheet according to the invention is relatively soft. In a preferred embodiment of the invention, the thermoplastic sheet has a shore D hardness of 10-30, preferably 15-29, more preferably 20-28, most preferably around 26. Shore D hardness is measured by methods available to a person skilled in the art. Measurement devices for measurement of the hardness of thermoplastic materials are commercially available, for instance from Mitutoyo.

Using methods known to a person skilled in the art, the sheet can be brought to a preferred thickness. In a preferred embodiment, the thermoplastic sheet has a thickness of 0.5 mm to 4 mm, preferably of 1 mm to 3 mm, more preferably of 1 mm to 2 mm.

In a preferred embodiment, the thermoplastic sheet is provided with perforations, preferably in a regular pattern. In a preferred embodiment, the sheet comprises an opening in the center of the sheet. This opening serves as orientation for the application of the sheet on a patient's head. Preferably the center of the sheet is positioned over the patient's nose.

The provision of perforations is advantageous as the perforations will reduce and/or avoid the patient some uncomfortable feelings such as sweating while the sheet of thermoplastic material is placed, for a certain time, on at least a part of his body.

Preferably the thermoplastic sheet has a tensile strength of at least 2 MPa, but less than 20 MPa. Sheets with such tensile strength show a minimum risk of tearing apart in normal circumstances of manual molding. These sheets show improved moldability and may be molded in such a way that they fit more closely to the anatomic shape of the body part to be immobilized than could be achieved up to now, without losing comfort. Preferred the thermoplastic sheet have an ultimate tensile strength which is between 2 and 15 MPa. With tensile strength is meant the tensile strength measured according to ASTM 683 method.

In a preferred embodiment a sheet can be manipulated to obtain between two to four times its original surface area, preferably three times.

Preferably the sheet of thermoplastic material have a flexural modulus which is sufficiently high but not too high, to provide functional mobility of the immobilization device. Thereto, the flexural modulus is preferably comprised between 5 and 37 MPa, more preferably between 7 and 35 MPa as determined with ASTM method D790.

A sheet obtained with a composition according to an embodiment of the invention has improved properties. In a particular is shows reduced draping when warmed in relation to sheets of the prior art. In the prior art, gamma irradiation is often applied to thermoplastic sheets in order to avoid the draping effect of a heated sheet. Radiation treatment is dispensable with sheets of the invention. Another technique used in the prior art to counteract the draping of a sheet is the application of a coating of for instance a polyurethane polymer on the sheet. Coating of a sheet according to an embodiment of the invention, is no longer required. Sheets produced from a composition according to the invention display reduced draping or sagging. The risk that they are damaged during transport is reduced. Although warming of the sheet above the glass transition temperature will cause the sheet to become stretchable and deformable it can be transported without damage by taking hold of the edges of the sheet and displacing it towards a patient.

In a further aspect, the invention relates to casts for surgical, orthopedic, radiotherapeutic or like use on human or animal subjects. More particularly, the invention relates to casts made from thermoplastic polymeric materials provided by the invention. The term "cast" as used herein, is used without intending limitation to any particular method of formation of the shape of the cast. A cast according to the invention is preferably a medical cast, more preferably a medical cast for use in radiotherapy such as radiation masks. Preferably the radiation mask is a face-mask.

Casts formed from the thermoplastic polymeric sheets, which sheets have the property of being shapeable initially, and deformable for removal if required, at a temperature not unduly uncomfortable for the subject and providing a suitably firm support at ambient temperature are provided by the invention.

In a further preferred embodiment, a cast further comprises perforations. This has for effect that skin breathing is not hampered after applying the sheet. The perforations have a diameter comprised between 0.5 mm and 2 mm and preferably about 1 to 1.3 mm. Said perforations may lie on rows separated by 1.5 mm to 4 mm. The skin may still breathe even after application of the material. The perforations represent 20% to 80%, preferably 30% to 70%, more preferably 40% to 60% of the device surface.

In another preferred embodiment, a cast has a thickness comprised between 0.5 mm and 4 mm, preferably between 1 mm and 3 mm, more preferably between 1 mm and 2 mm.

In a preferred embodiment, the cast is transparent. This has for effect that much of the light that falls on the cast is transmitted through it without being reflected. The inventors have found that the mixture of styrene acrylonitrile copolymer and the polycaprolactone is optically transparent and moldable at low temperature direct on a patient. This is renders a cast according to an embodiment of this invention particularly suitable for use in radiation therapy and diagnostic imaging and in all other applications where an accurate re-positioning of the immobilization device in intermittent treatments is of utmost importance. The optical transparency permits using positioning markers on one or both of the immobilization device and the body part to facilitate re-positioning.

The cast of this invention shows limited shrinking when cooling down from the molten or activated state. The degree of shrinking has been found significantly smaller than that observed with other materials known from the art. This is particularly advantageous as it permits minimizing the risk of a too tight fitting and the ensuing need to re-molding of the device, as well as the risk to sensing of excessive pressure or compression to the immobilized body part. This is an advantage over known prior art materials which usually show significant shrinking during crystallization while cooling.

Besides that, once molded, the immobilization device of this invention has been found to provide improved comfort to the patient because it feels soft to the skin; it also has a higher elasticity even after complete crystallization as compared to the casts and immobilization devices thereof known hitherto. As a consequence, the material may easily be cut with good and smooth finishing edges using conventional tools such as scissors and knives.

In a preferred embodiment of a thermoplastic sheet or medical cast of the invention, an identification element, such as a radio frequency identification tag, is provided on the sheet or cast. This is advantageous as it allows storage of information such as a patient's identity or medical record data.

In a further aspect, uses are provided for a medical cast according to an embodiment of the invention. Preferably a medical cast of the invention is used for delivering radiation therapy to a subject, preferably a human, in need thereof. Preferably the cast is a radiation mask.

In a preferred embodiment, the radiation mask of the invention has a shore D hardness which is at least twice the shore D hardness of the thermoplastic sheet. Preferably the shore D hardness of the mask is 40-60; preferably around 55.

Preferably the cast, in particular the radiation mask, is part of an immobilization assembly or device.

In a further aspect, the invention provides a method for the preparation of a thermoplastic composition according to an embodiment of the invention, comprising:
- a first heating step wherein a polymeric component comprising 20 to 40 weight % styrene acrylonitrile copolymer and 80 to 60 weight % polycaprolactone, optionally together with a first filler, is heated to a temperature of 100° C.-300° C., and
- a second heating step wherein the mixture obtained from the first heating step, optionally together with a cross-linker and/or a second filler, is heated to a temperature of 50° C. to 250° C.

In a preferred embodiment, the polymeric component is extruded. Using an extrusion process for the heating step(s) is advantageous as it provides optimized mixing and homogenization of the styrene acrylonitrile copolymer and polycaprolactone.

In a preferred embodiment, the composition is prepared in a sheet extruder resulting in a thermoplastic sheet.

It is preferred that the thermoplastic sheet has a melt index which is between 1 and 50 g/10 min, preferably between 2 and 25 g/10 min. With melt index is meant the melt index measured according to ASTM D1238 test method at 190° C., 2.5 kg. The thermoplastic sheet viscosity in the melt is not too high, nor too low to permit processing by injection molding, compression molding and to use the thermoplastic sheet for direct molding.

The thermoplastic sheet has some, but limited crystallinity. The total crystallinity of the thermoplastic sheet is preferably less than 25%, more preferably less than 21%. Herein % of crystallinity is expressed as wt. % of crystalline part of thermoplastic sheet with respect to the total weight of thermoplastic sheet.

The thermoplastic sheet obtained from the process is cut into pieces having dimensions corresponding to the body part to be immobilized. When the face of a patient is to be immobilized, an extra opening in the thermoplastic sheet is provided. Said extra opening will correspond to the nose of the patient after molding of the thermoplastic sheet.

In a further embodiment, a cast according to an embodiment of the present invention is made of a mixture of at least two granulates, wherein the first granulate consists of a mixture of polycaprolactone and styrene acrylonitrile copolymer and the second granulate consists essentially of polycaprolactone.

In a first step, the first granulate is obtained from a mixture of a styrene acrylonitrile copolymer and polycaprolactone, which is extruded. Similarly, polycaprolactone is extruded as a second granulate. The two different types of granulates are then supplied to a sheet extruder apparatus in which they are melted and thereafter extruded.

The extruded thermoplastic sheet is perforated either before or after leaving the extruder apparatus. Exposure time in the extruder is between 1 and 20 minutes, preferably between 2 and 18 minutes, more preferably between 4 and 16 minutes. Preferably the temperature profile of the extruder ranges from 60° C., preferably 70° C., more preferably 80° C. on entering the extruder to no higher than 230° C., preferably 220° C., more preferably 210° C. on leaving the extruder. The rotation speed of the extruder is preferably comprised between 20 and 60 rotations per minute (RPM), more preferably between 30 and 50 RPM, most preferably about 40 RPM.

In a preferred embodiment of the method, the thermoplastic composition comprises 0.05-5% of filler and/or 0.05%-5% cross-linker. Use of a filler and/or cross-linker is advantageous as they enhance the processability of the composition and resulting sheet and provide improved toughness to a sheet of thermoplastic material. This has for effect that a thermoplastic sheet from a composition comprising a filler and/or cross-linker is fortified so that a sheet when wet, will be more easily transportable and breakage of the wet sheet due to sagging is reduced.

For use the sheets may be softened by warming it to a temperature above its glass transition temperature, for instance by immersion in warm water, at which temperature it becomes shapeable. In a preferred embodiment, the sheet is warmed by immersion in an aqueous liquid with a temperature between 70-90° C.

It is formed into a shape conforming to the contours of a part of a subject's body, either animal or human. Adjustment of the size of the sheet allows it to cover a desired part of the subject's body. By allowing the sheet, now in supportive relationship to the body part, to cool below its glass transition temperature, preferably to ambient temperature of 20° C.-30° C., it will rigidify and provide a form-fitting cast. The form-fitting cast is preferably a radiation mask, more preferably a face-mask.

A method of manufacturing a cast according to an embodiment of the invention preferably comprises the steps of: providing a thermoplastic composition of the invention in the form of a sheet, warming the sheet above its glass transition temperature thereby providing a sheet that is deformable into a shape conforming to the contours of a part of a subject's body, applying the warmed sheet to a part of a subject's body, thereby covering at least part of the subject's body, cooling the sheet to ambient temperature to rigidify and provide the cast.

The cast, preferably radiation mask, may be adopted further. For instance, the mask together with a fixation plate and connecting means for connecting the mask to the fixation plate may form an immobilization device. The fixation means are for connecting the mask to the fixation plate. The mask thereby covers at least part of the part of the patient to be immobilized. Preferably the immobilization device is adopted to immobilize a patient in need of radiotherapy.

An immobilization device of this invention is directly moldable on the human body and presents the advantage that it is unbreakable in case of hard handling or after falling. Also the immobilization device obtained after molding, such as a mask if the head is the patient's body part that needs to be immobilized, is elastic and returns to its shape after applying external forces that made it deform. Moreover, the immobilization device is optically transparent which gives the possibility to observe whether or not it has been properly molded to the body part.

An immobilization device according to the an embodiment of present invention has a relatively high bending modulus, good elasticity properties and high melt strength, which result in an immobilization device that is rubber-like when the thermoplastic sheet is in the molten state, which sheet may be stretched and shaped to optimize fit to the body part, at low risk to tearing apart. The high tensile strength permits making thin sheets, thus improving wearing comfort.

The inventors have also observed that an immobilization device of this invention shows a high elastic memory, in particular that it can be easily re-molded after having been molded for a first time. Re-molding is done by re-heating the device to the melting temperature of the material, followed by molding the material to the patient's body. The re-molding permits producing consecutive immobilization devices from one and the same starting device, and to gradually change the degree and position of immobilization with time. The fact that the material is re-moldable permits providing relief to positions where pressure is sensed by the patient after the immobilization device has been molded for a first time to fit to the body part that needs immobilization, and it permits correcting or complete re-molding the immobilization device in case it has been incorrectly molded or in case the position of the immobilized part needs to be changed in the course of time. The possibility to re-molding presents the advantage that the device is re-sizable and allows patient adaptation.

The inventors have further observed that the thermoplastic sheet according to the present invention, show a high impact resistance which results in an immobilization device with a good shock resistance, and a high tear strength even in the molten or partially cooled down state as a consequence of which there is a minimum risk to tearing apart of the sheet during and/or after manual molding.

The inventors have further observed that the thermoplastic sheet show excellent self-adhesion in a molten state but at the same time is non-sticky and does not stick to the skin neither to the hair of body part. This means that enclosing immobilization devices can be molded of one and the same material, without necessitating the use of adhesives or the provision of additional closure parts, such as for example Velcro(R). This simplifies production. On the other hand, the need of using release means such as talc or release film materials to be applied between the immobilization device and the skin, may be overcome.

The immobilization device of the present invention is suitable for use as a fixation device in radiation therapy and diagnostic imaging.

The present invention will now be illustrated by the following non-limitative examples.

EXAMPLES

Example 1

A thermoplastic sheet is extruded from a mixture containing:
34.5% of a granulate mixture of polycaprolactone and Luran®
65% polycaprolactone granulate
0.25% triallylcyanurate
and 0.25% talc.

Example 2

A thermoplastic sheet is extruded from a mixture containing:
55% polycaprolactone granulates
44.5% of a granulate mixture of polycaprolactone and Luran®
0.35% triallylcyanurate
and 0.15% talc.

Example 3

A thermoplastic sheet is extruded from a mixture containing:
60% polycaprolactone granulates
39.5% polycaprolactone/Luran mixture granulates
and 0.5% talc.

Example 4

A thermoplastic composition was prepared as follows. Luran 348Q granulate was mixed with polycaprolactone granulate thereby forming a mixture comprising at least 50 weight % polycaprolactone. Talc was added to the mixture. The resulting mixture was extruded and a granulate was obtained.

Part of the mixture was brought together with more polycaprolactone granulate. Additional amounts of filler were added. The filler can be another mineral substance, but it is preferably again talc. About 1% of triallylcyanurate cross-linker was added. The mixture thus obtained was warmed and formed into a sheet. When still warm, holes were punched into the sheet of 1-3 mm in diameter. The shore D hardness of the thermoplastic sheet obtained was 26.

The sheet was warmed in water of 70° C.-90° C. for approximately 1 minute. The sheet was removed from the liquid and dipped dry. The sheet was stretched to about 3 times its original size. The stretched sheet was still firm and hardly any sagging was observed. The sheet was transferred to a patient in need of radiotherapy in under 1 minute. By the time it reached the patient the temperature decreased to 35° C.

The sheet was applied to the facial skin. It was molded to take the contours of the head and forming a mask. During about 3 minutes the sheet was still soft enough to allow deformations. Thereafter it became rigid. The shore D hardness of the mask obtained from the sheet after was measured when the hardening was complete. It was 54.7. The mask was sufficiently stiff around the nose and jaw of the patient so that further reinforcement of the mask could be dispensed with. As the mask still has some flexibility it was easily removed for later use. The personalized mask produced provided an improved fit. The mask was transparent enabling the positioning of the patient and/or radiation mark for radiotherapeutic treatment of a tumor.

What is claimed is:

1. A thermoplastic sheet comprising a thermoplastic composition for forming a cast, said composition having a polymeric component comprising a mixture of a styrene acrylonitrile copolymer and polycaprolactone, wherein the polymeric component comprises, 20 to 40 weight % of a styrene acrylonitrile copolymer and 80 to 60 weight % of a polycaprolactone, expressed in weight % of the polymeric component, wherein the thermoplastic composition further comprises a filler, and wherein the thermoplastic composition has a glass transition temperature of 35° C.-80° C., and a shore D hardness of 10-30, and wherein said thermoplastic sheet is provided with perforations.

2. Thermoplastic sheet according to claim 1, wherein the filler of the thermoplastic composition is talc.

3. Thermoplastic sheet according to claim 1, wherein the thermoplastic composition has a glass transition temperature between 45° C. and 70° C.

4. Thermoplastic sheet according to claim 1, with a thickness of 0.5 mm to 4 mm.

5. Thermoplastic sheet according to claim 1, which is transparent.

6. Thermoplastic sheet according to claim 1, wherein the perforations are provided in a regular pattern.

7. Thermoplastic sheet according to claim 1, comprising an identification element.

8. Thermoplastic sheet according to claim 1, wherein the thermoplastic composition has a glass transition temperature between 55° C. and 65° C.

9. Thermoplastic sheet according to claim 1, with a thickness of 1 mm to 3 mm.

10. Thermoplastic sheet according to claim 1, with a thickness of 1 mm to 2 mm.

11. Thermoplastic sheet according to claim 1, wherein the thermoplastic sheet further comprises a radio frequency identification tag.

12. Thermoplastic sheet according to claim 1, wherein said thermoplastic composition comprises 0.05-5 weight % of filler.

13. Thermoplastic sheet according to claim 1, wherein said thermoplastic composition further comprises a cross-filler.

14. Thermoplastic sheet according to claim 13, wherein said thermoplastic composition comprises 0.05-5 weight % of cross-linker.

15. Thermoplastic sheet according to claim 13, wherein said cross-linker is triallylcyanurate.

16. Thermoplastic sheet according to claim 1, wherein the sheet comprises an opening in the center of the sheet for orientation of the sheet on a patient's head.

17. Thermoplastic sheet according to claim 1, wherein the perforations comprise a diameter between 0.5 mm and 2 mm.

18. Method for the preparation of a thermoplastic sheet according to claim 1, comprising:
  mixing 20 to 40 weight % styrene acrylonitrile copolymer with 80 to 60 weight % polycaprolactone thereby providing a polymeric component,
  optionally adding to the polymeric component a first filler,
  granulating said polymeric component optionally together with the first filler thereby providing a first granulate,
  adding to the first granulate a polycaprolactone granulate and optionally a cross-linker and/or a second filler,
  bringing the resulting mixture under the action of pressure or heat or both in the form of a thermoplastic sheet, and
  perforating the thermoplastic sheet.

19. Method according to claim 18, wherein the thermoplastic composition comprises 0.05-5% of filler and/or 0.05%-5% cross-linker.

20. Method according to claim 18, wherein the filler is talc and the cross-linker is triallylcyanurate.

21. A method for manufacturing a radiation mask for delivering radiotherapy to a subject in need thereof, comprising the steps of:
  providing a thermoplastic sheet according to claim 1,
  warming the sheet above its glass transition temperature thereby providing a sheet that is stretchable,
  stretching the stretchable sheet to obtain a stretched sheet with a surface area at least double the surface area of the stretchable sheet,
  applying the stretched sheet to at least part of the subject's body in need of radiotherapy thereby deforming the stretched sheet into a shape conforming to the part of subject's body, and
  cooling the deformed sheet to ambient temperature to rigidify the deformed sheet and provide the radiation mask.

22. A radiation mask formed from a thermoplastic composition having a polymeric component comprising 20 to 40 weight % of a styrene acrylonitrile copolymer and 80 to 60 weight % of a polycaprolactone, expressed in weight% of the polymeric component, wherein the thermoplastic composition further comprises a filler, and wherein the thermoplastic composition has a glass transition temperature of 35° C.-80° C., wherein the radiation mask comprises a shore D hardness of 40-60, and wherein said radiation mask is provided with perforations.

23. Radiation mask according to claim 17, wherein the radiation mask comprises a radio frequency identification tag.

24. A method for delivering radiotherapy to a subject in need thereof, comprising administering the radiation mask of claim 22 to the subject.

25. A method for manufacturing a radiation mask for delivering radiotherapy to a subject in need thereof, comprising the steps of:
  providing a thermoplastic sheet according to claim 1;
  warming the sheet above its glass transition temperature thereby providing a sheet that is stretchable;
  stretching the stretchable sheet to obtain a stretched sheet with a surface area at least double the surface area of the stretchable sheet;
  applying the stretched sheet to at least part of the subject's body in need of radiotherapy thereby deforming the stretched sheet into a shape conforming to the part of the subject's body; and
  cooling the deformed sheet to ambient temperature to rigidify the deformed sheet and provide the radiation mask.

* * * * *